(12) United States Patent  
Giamis (10) Patent No.: US 8,937,287 B2  
(45) Date of Patent: Jan. 20, 2015

(54) SELF-REFERENCING RADIATION DETECTOR FOR USE WITH A RADIOPHARMACEUTICAL QUALITY CONTROL TESTING SYSTEM

(75) Inventor: Anthony M. Giamis, Green Oaks, IL (US)

(73) Assignee: ABT Molecular Imaging, Inc., Knoxville, TN (US)

( * ) Notice: Subject to any disclaimer, the term of this patent is extended or adjusted under 35 U.S.C. 154(b) by 407 days.

(21) Appl. No.: 13/451,295

(22) Filed: Apr. 19, 2012

(65) Prior Publication Data

US 2013/0277566 A1    Oct. 24, 2013

(51) Int. Cl.  
*G01J 1/42* (2006.01)

(52) U.S. Cl.  
USPC .......................................................... 250/393

(58) Field of Classification Search  
CPC .......................... G01N 2030/77; G01N 30/62  
USPC .......................................................... 250/393  
See application file for complete search history.

(56) References Cited

U.S. PATENT DOCUMENTS

| | | | |
|---|---|---|---|
| 4,187,076 A | 2/1980 | Elsohly et al. | |
| 6,270,982 B1 | 8/2001 | Jordan et al. | |
| 6,391,570 B1 | 5/2002 | Jordan et al. | |
| 7,235,216 B2 | 6/2007 | Kiselev et al. | |
| 7,329,538 B2 | 2/2008 | Wainwright et al. | |
| 7,479,375 B2 | 1/2009 | Wainwright et al. | |
| 7,734,331 B2 | 6/2010 | Dhawale et al. | |
| 2002/0048536 A1 | 4/2002 | Bergh et al. | |
| 2005/0232861 A1 | 10/2005 | Buchanan et al. | |
| 2006/0253259 A1 | 11/2006 | Fernandez | |
| 2008/0064110 A1 | 3/2008 | Elizarov et al. | |
| 2008/0067413 A1 | 3/2008 | Nutt | |
| 2008/0233018 A1 | 9/2008 | van Dam et al. | |
| 2008/0242915 A1 | 10/2008 | Jackson et al. | |
| 2009/0036668 A1 | 2/2009 | Elizarov et al. | |

(Continued)

FOREIGN PATENT DOCUMENTS

WO    WO 2011/028552    3/2011  
WO    WO 2013/012808    1/2013

OTHER PUBLICATIONS

J. Koziorowski, "A simple method for the quality control of [18F]FDG", Applied radiation and isotopes 68 (2010) 1740-1742.*

(Continued)

*Primary Examiner* — David Porta  
*Assistant Examiner* — Mindy Vu  
(74) *Attorney, Agent, or Firm* — Pitts & Lake, P.C.

(57) ABSTRACT

A self-referencing radiation detector to test the radiochemical purity of a sample radiopharmaceutical solution. In some embodiments, the self-referencing radiation detector measures the radioactivity of a sample radiopharmaceutical solution before the sample radiopharmaceutical solution is passed through a high performance liquid chromatography column. The radiation detector then measures the radioactivity of each separated molecularly distinct species from the high performance liquid chromatography column. The radiochemical purity of the sample radiopharmaceutical solution is calculated by comparing the measured radioactivity of separated molecularly distinct species from said high performance liquid chromatography column to the measured radioactivity of the sample radiopharmaceutical solution before the sample radiopharmaceutical solution is passed through the high performance liquid chromatography column.

8 Claims, 3 Drawing Sheets

(56) References Cited

U.S. PATENT DOCUMENTS

| | | |
|---|---|---|
| 2010/0145630 A1 | 6/2010 | Ball et al. |
| 2011/0070158 A1 | 3/2011 | Nutt et al. |
| 2011/0070160 A1 | 3/2011 | Nutt et al. |
| 2011/0178359 A1 | 7/2011 | Hirschman et al. |
| 2013/0023657 A1* | 1/2013 | Klausing et al. .............. 536/28.2 |

OTHER PUBLICATIONS

Unknown: Lesson 6: Dectors for HPLC, Internet Citation, Aug. 2, 2013 XP002708717, http://www.shodex.net/?lang+2&applic=1485.

James M. Miller, Chromatography—Concepts and Contrasts Wiley-Interscience, pp. 278-284, Jan. 1, 2005 XP002708718.

* cited by examiner

SELF-REFERENCING RADIATION DETECTOR FOR USE WITH A RADIOPHARMACEUTICAL QUALITY CONTROL TESTING SYSTEM

CROSS-REFERENCE TO RELATED APPLICATIONS

Not Applicable

STATEMENT REGARDING FEDERALLY-SPONSORED RESEARCH OR DEVELOPMENT

Not Applicable

BACKGROUND OF THE INVENTION

1. Field of Invention

This invention relates to radiation detectors and methods for detecting and measuring radioactivity in chemical sample. In particular, the present general inventive concept relates to devices, systems and methods for analyzing the radioactivity of organic synthetic pharmaceuticals.

2. Description of the Related Art

A biomarker is used to interrogate a biological system and can be created by "tagging" or labeling certain molecules, including biomolecules, with a radioisotope. A biomarker that includes a positron-emitting radioisotope is required for positron-emission tomography (PET), a noninvasive diagnostic imaging procedure that is used to assess perfusion or metabolic, biochemical and functional activity in various organ systems of the human body. Because PET is a very sensitive biochemical imaging technology and the early precursors of disease are primarily biochemical in nature, PET can detect many diseases before anatomical changes take place and often before medical symptoms become apparent. PET is similar to other nuclear medicine technologies in which a radiopharmaceutical is injected into a patient to assess metabolic activity in one or more regions of the body. However, PET provides information not available from traditional imaging technologies, such as magnetic resonance imaging (MRI), computed tomography (CT) and ultrasonography, which image the patient's anatomy rather than physiological images. Physiological activity provides a much earlier detection measure for certain forms of disease, cancer in particular, than do anatomical changes over time.

A positron-emitting radioisotope undergoes radioactive decay, whereby its nucleus emits positrons. In human tissue, a positron inevitably travels less than a few millimeters before interacting with an electron, converting the total mass of the positron and the electron into two photons of energy. The photons are displaced at approximately 180 degrees from each other, and can be detected simultaneously as "coincident" photons on opposite sides of the human body. The modern PET scanner detects one or both photons, and computer reconstruction of acquired data permits a visual depiction of the distribution of the isotope, and therefore the tagged molecule, within the organ being imaged.

Most clinically-important positron-emitting radioisotopes are produced in a cyclotron. Cyclotrons operate by accelerating electrically-charged particles along outward, quasi-spherical orbits to a predetermined extraction energy generally on the order of millions of electron volts. The high-energy electrically-charged particles form a continuous beam that travels along a predetermined path and bombards a target. When the bombarding particles interact in the target, a nuclear reaction occurs at a sub-atomic level, resulting in the production of a radioisotope. The radioisotope is then combined chemically with other materials to synthesize a radiochemical or radiopharmaceutical (hereinafter "radiopharmaceutical") suitable for introduction into a human body. The cyclotrons traditionally used to produce radioisotopes for use in PET have been large machines requiring great commitments of physical space and radiation shielding. These requirements, along with considerations of cost, made it unfeasible for individual hospitals and imaging centers to have facilities on site for the production of radiopharmaceuticals for use in PET.

Thus, in current standard practice, radiopharmaceuticals for use in PET are synthesized at centralized production facilities. The radiopharmaceuticals then must be transported to hospitals and imaging centers up to 200 miles away. Due to the relatively short half-lives of the handful of clinically important positron-emitting radioisotopes, it is expected that a large portion of the radioisotopes in a given shipment will decay and cease to be useful during the transport phase. To ensure that a sufficiently large sample of active radiopharmaceutical is present at the time of the application to a patient in a PET procedure, a much larger amount of radiopharmaceutical must be synthesized before transport. This involves the production of radioisotopes and synthesis of radiopharmaceuticals in quantities much larger than one (1) unit dose, with the expectation that many of the active atoms will decay during transport.

The need to transport the radiopharmaceuticals from the production facility to the hospital or imaging center (hereinafter "site of treatment") also dictates the identity of the isotopes selected for PET procedures. Currently, fluorine isotopes, and especially fluorine-18 (or F-18) enjoy the most widespread use. The F-18 radioisotope is commonly synthesized into $[^{18}F]$fluorodeoxyglucose, or $[^{18}F]$FDG, for use in PET. F-18 is widely used mainly because its half-life, which is approximately 110 minutes, allows for sufficient time to transport a useful amount. The current system of centralized production and distribution largely prohibits the use of other potential radioisotopes. In particular, carbon-11 has been used for PET, but its relatively short half-life of 20.5 minutes makes its use difficult if the radiopharmaceutical must be transported any appreciable distance. Similar considerations largely rule out the use of nitrogen-13 (half-life: 10 minutes) and oxygen-15 (half-life: 2.5 minutes).

As with any medical application involving the use of radioactive materials, quality control is important in the synthesis and use of PET biomarker radiopharmaceuticals, both to safeguard the patient and to ensure the effectiveness of the administered radiopharmaceutical. For example, for the synthesis of $[^{18}F]$FDG from mannose triflate, a number of quality control tests exist. The final $[^{18}F]$FDG product should be a clear, transparent solution, free of particulate impurities; therefore, it is important to test the color and clarity of the final radiopharmaceutical solution. The final radiopharmaceutical solution is normally filtered through a sterile filter before administration, and it is advisable to test the integrity of that filter after the synthesized radiopharmaceutical solution has passed through it. The acidity of the final radiopharmaceutical solution must be within acceptable limits (broadly a pH between 4.5 and 7.5 for $[^{18}F]$FDG, although this range may be different depending upon the application and the radiopharmaceutical tracer involved). The final radiopharmaceutical solution should be tested for the presence and levels of volatile organics, such as ethanol or methyl cyanide, that may remain from synthesis process. Likewise, the solution should be tested for the presence of crown ethers or other reagents used in the synthesis process, as the presence of these reagents in the final dose is problematic. Further, the radiochemical purity of the final solution should be tested to ensure that it is sufficiently high for the solution to be useful. Other tests, such as tests of radionuclide purity, tests for the presence of bacterial endotoxins, and tests of the sterility of the synthesis system, are known in the art.

At present, most or all of these tests are performed on each batch of radiopharmaceutical, which will contain several doses. The quality control tests are performed separately by human technicians, and completing all of the tests typically requires between 45 and 60 minutes.

BRIEF SUMMARY OF THE INVENTION

As disclosed herein, in several example embodiments, the present general inventive concept comprises self-referencing radiation detectors for use with quality control systems incorporating high performance liquid chromatography (HPLC) to perform quality control testing on a radiopharmaceutical solution shortly after synthesis.

In some embodiments, a self-referencing radiation detector according to the present general inventive concept measures the radioactivity of a sample radiopharmaceutical solution before the sample radiopharmaceutical solution is passed through a high performance liquid chromatography column. The radiation detector then measures the radioactivity of each separated molecularly distinct species from the high performance liquid chromatography column. The radiochemical purity of the sample radiopharmaceutical solution is calculated by comparing the measured radioactivity of separated molecularly distinct species from said high performance liquid chromatography column to the measured radioactivity of the sample radiopharmaceutical solution before the sample radiopharmaceutical solution is passed through the high performance liquid chromatography column.

In some embodiments, a self-referencing radiation detector is used in conjunction with an HPLC column in a quality control system to perform quality control testing on a sample radiopharmaceutical solution. First, the self-referencing radiation detector measures the radioactivity of the sample radiopharmaceutical solution before the sample radiopharmaceutical solution enters the HPLC column. Next, the sample radiopharmaceutical solution enters the HPLC column, where a number of components of the sample radiopharmaceutical solution are separated by their differing retention times into separate molecularly distinct components. The, the self-referencing radiation detector measures the radioactivity of each separate molecularly distinct component that is eluted from the HPLC column. Acquiring a measurement of radioactivity of each separate molecularly distinct component eluted from the HPLC column, and comparing the acquired measurements to the measured radioactivity of the sample radiopharmaceutical solution taken before the sample radiopharmaceutical solution entered the HPLC column, makes possible a calculation of the radiochemical identity and radiochemical purity of the sample radiopharmaceutical solution.

In some embodiments, a self-referencing radiation detector first measures the radioactivity (or, simply, "activity") of the sample radiopharmaceutical solution before the sample radiopharmaceutical solution enters the HPLC column—i.e., when the constituent components of the sample radiopharmaceutical solution are still present in an unseparated bolus. Measurement of the activity of the bolus before the sample radiopharmaceutical solution enters the HPLC column gives a value for the activity of the bolus. Next, the bolus of sample radiopharmaceutical solution enters the HPLC column, where a number of components of the sample radiopharmaceutical solution are separated by their differing retention times into separate molecularly distinct components. The separate molecularly distinct components then elute from the HPLC column after their distinct retention times. For each separate molecularly distinct component, the retention time of that component is noted, and the self-referencing radiation detector measures the activity of that component to produce a raw activity measurement for that component. Because the radioisotopes present in the sample radiopharmaceutical solution continue to decay while passing through HPLC column, the raw activity measurement for each component is "corrected" by using the raw activity measurement for the component, the retention time for that component, and the half-life of the radioisotope to produce a decay-corrected activity value for that component. A comparison of the decay-corrected activity value for the separate components with the measured activity of the bolus provides a quantification of the radiochemical identity and radiochemical purity of the sample radiopharmaceutical solution.

In some embodiments, the present general inventive concept embraces a system to test the radiochemical purity of a sample radiopharmaceutical solution, the system comprising a high performance liquid chromatography column to receive the sample radiopharmaceutical solution and to separate molecularly distinct species within the sample radiopharmaceutical solution into a number of separated molecularly distinct species; and a radiation detector, said radiation detector measuring the radioactivity of the sample radiopharmaceutical solution before the sample radiopharmaceutical solution is received by said high performance liquid chromatography column, said radiation detector measuring the radioactivity of each separated molecularly distinct species from said high performance liquid chromatography column. In some embodiments, the system further comprises a refractive index detector to measure the amount of each separated molecularly distinct species from said high performance liquid chromatography column. In some embodiments, the system further comprises an ultraviolet-light detector to measure the optical qualities of the separated molecularly distinct species from said high performance liquid chromatography column. In some embodiments, the system further comprises a computer to operate a program to calculate a decay-corrected radioactivity measurement for each separated molecularly distinct species using the measurement of the radioactivity of each separated molecularly distinct species from said high performance liquid chromatography column, the half-life of a selected radioactive isotope within the radiopharmaceutical solution, and the time elapsed between measuring the radioactivity of the sample radiopharmaceutical solution before the sample radiopharmaceutical solution is received by said high performance liquid chromatography column and measuring the radioactivity of each separated molecularly distinct species from said high performance liquid chromatography column, whereby the radiochemical purity of the sample radiopharmaceutical solution is calculated by comparing the decay-corrected radioactivity measurements of the separated molecularly distinct species to the radioactivity measurement of the sample radiopharmaceutical solution.

In some embodiments, the present general inventive concept embraces a method to test the radiochemical purity of a sample radiopharmaceutical solution including a selected radioactive isotope, comprising: acquiring with a radiation detector a radioactivity measurement of the sample radiopharmaceutical solution; passing the sample radiopharmaceutical solution high performance liquid chromatography column to separate molecularly distinct species within the sample radiopharmaceutical solution into a number of separated molecularly distinct species that elute from said high performance liquid chromatography column with distinct retention times; acquiring with said radiation detector an uncorrected radioactivity measurement for each separated molecularly distinct species eluted from said high performance liquid chromatography column; and calculating a decay-corrected radioactivity measurement for each separated molecularly distinct species using the uncorrected radioactivity measurement, the half-life of the selected radioactive isotope, and the time elapsed between the acquisition of the radioactivity measurement of the sample radiopharmaceutical solution the acquisition of the uncorrected radioactivity measurement for that separated molecularly distinct species, whereby the radiochemical purity of the sample radiopharmaceutical solution is calculated by comparing the decay-corrected radioactivity measurements of the separated molecularly distinct species to the radioactivity measurement of the sample radiopharmaceutical solution. In some embodiments, the method further comprises passing the separated molecularly distinct species through a refractive index detector to measure the amount of each separated molecularly distinct species eluted from said high performance liquid chromatography column. In some embodiments, the method further comprises passing the separated molecularly distinct species through an ultraviolet-light detector to measure the optical qualities of the separated molecularly distinct species eluted from said high performance liquid chromatography column. In some embodiments, the method further comprises passing the sample radiopharmaceutical solution through an ultraviolet-light detector to measure the optical qualities of the sample radiopharmaceutical solution. In some embodiments, the method further comprises a computer to operate a program to calculate the decay-corrected radioactivity measurement for each separated molecularly distinct species.

In some embodiments, the selected radioisotope is selected from the group consisting of carbon-11, nitrogen-13, oxygen-15, and fluorine-18. In some embodiments, the separated molecularly distinct species eluted from said high performance liquid chromatography column is [$^{18}$F]-2-fluoro-2-deoxy-D-glucose. However, it is not the intention of the applicant to restrict or in any way limit the scope of the present invention to the identified radioactive isotopes or to any specific radiopharmaceutical compound, solution, or mixture. Additional modifications will appear to those skilled in the art and are embraced by the present general inventive concept.

BRIEF DESCRIPTION OF THE SEVERAL VIEWS OF THE DRAWINGS

The above-mentioned features and other features of the present general inventive concept will become more clearly understood from the following detailed description of the invention read together with the drawings in which.

DETAILED DESCRIPTION OF THE INVENTION

Self-referencing radiation detectors for use with quality control systems incorporating high performance liquid chromatography (HPLC) to perform quality control testing on a sample radiopharmaceutical solution are described more fully hereinafter. This invention may, however, be embodied in many different forms and should not be construed as limited to the embodiments set forth herein. Rather, these embodiments are provided to ensure that this disclosure is thorough and complete, and to ensure that it fully conveys the scope of the invention to those skilled in the art.

In some embodiments, a self-referencing radiation detector is used in conjunction with an HPLC column in a quality control system to perform quality control testing on a sample radiopharmaceutical solution. First, the self-referencing radiation detector measures the radioactivity of the sample radiopharmaceutical solution before the sample radiopharmaceutical solution enters the HPLC column. Next, the sample radiopharmaceutical solution enters the HPLC column, where a number of components of the sample radiopharmaceutical solution are separated by their differing retention times into separate molecularly distinct components. The, the self-referencing radiation detector measures the radioactivity of each separate molecularly distinct component that is eluted from the HPLC column. Acquiring a measurement of radioactivity of each separate molecularly distinct component eluted from the HPLC column, and comparing the acquired measurements to the measured radioactivity of the sample radiopharmaceutical solution taken before the sample radiopharmaceutical solution entered the HPLC column, makes possible a calculation of the radiochemical identity and radiochemical purity of the sample radiopharmaceutical solution.

In some embodiments, a self-referencing radiation detector first measures the radioactivity (or, simply, "activity") of the sample radiopharmaceutical solution before the sample radiopharmaceutical solution enters the HPLC column—i.e., when the constituent components of the sample radiopharmaceutical solution are still present in an unseparated bolus. Measurement of the activity of the bolus before the sample radiopharmaceutical solution enters the HPLC column gives a value $A_B$ for the activity of the bolus. Next, the bolus of sample radiopharmaceutical solution enters the HPLC column, where a number of components of the sample radiopharmaceutical solution are separated by their differing retention times into separate molecularly distinct components. The separate molecularly distinct components then elute from the HPLC column after their distinct retention times. For each separate molecularly distinct component, the retention time of that component is noted, and the self-referencing radiation detector measures the activity of that component to produce a raw activity measurement for that component. Because the radioisotopes present in the sample radiopharmaceutical solution continue to decay while passing through HPLC column, the raw activity measurement for each component is "corrected" by using the raw activity measurement for the component, the retention time for that component, and the half-life of the radioisotope to produce a decay-corrected activity value for that component. A comparison of the decay-corrected activity value for the separate components with the measured activity of the bolus provides a quantification of the radiochemical identity and radiochemical purity of the sample radiopharmaceutical solution.

Thus, in one example embodiment of the present general inventive concept, a sample radiopharmaceutical solution including [$^{18}$F]-2-fluoro-2-deoxy-D-glucose (hereinafter [$^{18}$F]FDG) is tested.

First, self-referencing radiation detector measures the activity of the sample radiopharmaceutical solution before the sample radiopharmaceutical solution enters the HPLC column, providing $A_B$.

Second, the sample radiopharmaceutical solution enters the HPLC column. A number of components of the sample radiopharmaceutical solution are separated by their differing retention times into separate molecularly distinct components. In the case of a sample radiopharmaceutical solution from the synthesis of [$^{18}$F]FDG, common molecularly distinct components in the solution generally include [$^{18}$F]-2-fluoro-1,3,4,6-tetra-O-acetyl-D-glucose (hereinafter [$^{18}$F] FTAG) (a common byproduct of the synthesis of [$^{18}$F]FDG) and unreacted F-18 fluorine (including unreacted F-18 fluoride ions). The separate molecularly distinct components elute from the HPLC column after their distinct retention times.

Third, the self-referencing radiation detector measures the activity of each separate molecularly distinct component that is eluted from the HPLC column. In this example embodiment, the self-referencing radiation detector measures the activity of the [$^{18}$F]FTAG, the [$^{18}$F]FDG, and the unreacted F-18 fluorine, obtaining three raw activity measurements: $A_{FTAG}$ for [$^{18}$F]FTAG, $A_{FDG}$ for [$^{18}$F]FDG, and $A_F$ for the unreacted F-18 fluorine. For each of the eluted separate molecularly distinct components—the [$^{18}$F]FTAG, the [$^{18}$F]FDG, and the unreacted F-18 fluorine—the raw activity measurement for each component is "corrected" by using the raw activity measurement for the component, the retention time for that component, and the half-life of the radioisotope to produce a decay-corrected activity for that component. Thus, correction of the raw activity measurements gives three decay-corrected activity values: $A^*_{FTAG}$ for [$^{18}$F]FTAG, $A^*_{FDG}$ for [$^{18}$F]FDG, and $A^*_F$ for the unreacted F-18 fluorine.

In some embodiments, the radiochemical purity of the sample radiopharmaceutical solution is calculated as a ratio of the decay-corrected activity value for the desired radiopharmaceutical component (in some example embodiments, [$^{18}$F]FDG, for instance) to the activity measurement of the bolus, taken before the sample radiopharmaceutical solution entered the HPLC column. Thus, in some example embodiments, the radiochemical purity $R_P$ of the sample radiopharmaceutical solution is given as $$R_P = A^*_{FDG}/A_B$$

In some embodiments, the radiochemical purity $R_P$ of the sample radiopharmaceutical solution is calculated as a ratio of the decay-corrected activity value for the desired radiopharmaceutical component (for example, [$^{18}$F]FDG) to the sum of the decay-corrected activity values for all of the separate molecularly distinct components eluted from the HPLC column:

$$R_P = A^*_{FDG}/(A^*_{FDG} + A^*_{FTAG} + A^*_F)$$

In some embodiments, the radiochemical purity is expressed as a percentage.

Acquiring a measurement of radioactivity of each separate molecularly distinct species eluted from the HPLC column, and comparing the acquired measurements to the measured radioactivity of the sample radiopharmaceutical solution taken before the sample radiopharmaceutical solution entered the HPLC column, makes possible a calculation of the radiochemical identity and radiochemical purity of the sample radiopharmaceutical solution.

Although the present general inventive concept has been illustrated by description of an example embodiment where the desired radiopharmaceutical component is [$^{18}$F]FDG, the present invention is not limited to embodiments in which [$^{18}$F]FDG is the desired radiopharmaceutical component. In some embodiments of the present general inventive concept, the radioisotope is selected from the group consisting of carbon-11, nitrogen-13, oxygen-15, and fluorine-18.

Figure 1:
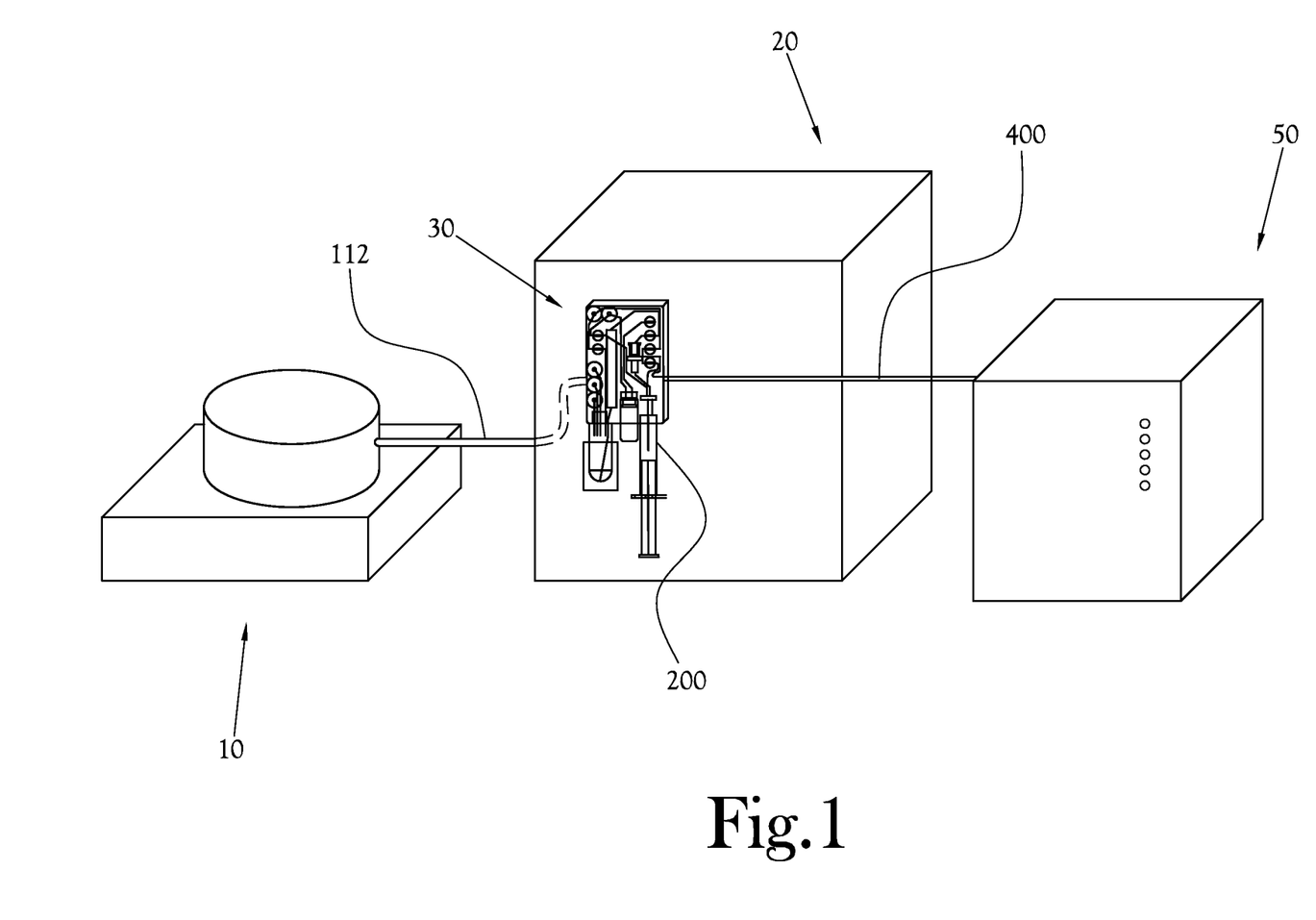
FIG. 1 is an schematic illustration of one example embodiment of the present general inventive concept, showing an overview of a PET biomarker production system, including the accelerator, the chemical production module (CPM), the dose synthesis module (DSM), and the quality control module (QCM)

In some of the example embodiments described below, a self-referencing radiation detector operates as part of an HPLC-based quality control module, which in turn is one part of a larger PET biomarker production system that also comprises a chemical production module and a dose synthesis module. In one example embodiment, illustrated in FIG. 1, a PET biomarker production system comprises an accelerator 10, which produces the radioisotopes; a chemical production module (or CPM) 20; a dose synthesis module (or DSM) 30; and an HPLC-based quality control module (or QCM) 50. Once the accelerator 10 has produced a radioisotope, the radioisotope travels via a radioisotope delivery tube 112 to the DSM 30 attached to the CPM 20. The CPM 20 holds reagents and solvents that are required during the radiopharmaceutical synthesis process. In the DSM 30, the radiopharmaceutical solution is synthesized from the radioisotope and then purified for testing and administration. Following synthesis and purification, a portion (the "sample portion") of the resultant radiopharmaceutical solution is transported by way of a quality-control transfer line 400 to the QCM 50, and another portion flows into a dose vessel 200. Within the QCM 50, a number of diagnostic instruments perform automated quality control tests on the sample portion.

Figure 2:
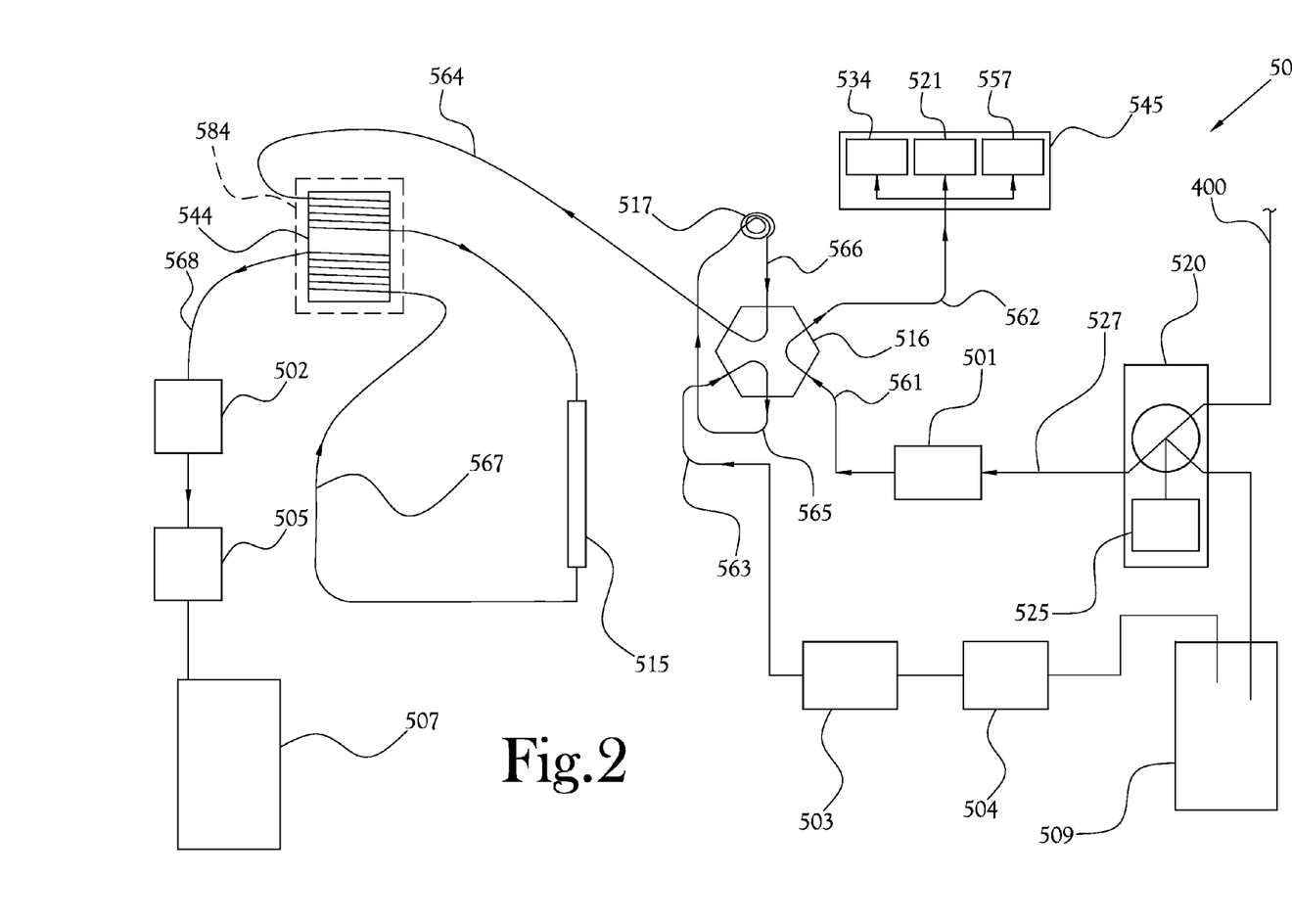
FIG. 2 is a first flow diagram illustration of an example embodiment of an HPLC-based QCM incorporating a self-referencing radiation detector according to the present general inventive concept, showing an injection valve in a first state.

FIG. 2 shows a flow chart illustrating one example embodiment of an HPLC-based QCM 50 with a self-referencing radiation detector 544 according to the present general inventive concept. The example HPLC-based QCM 50 illustrated in FIG. 2 is to test a first portion of purified radiopharmaceutical solution (hereinafter "the sample radiopharmaceutical solution" or simply "sample") from a DSM. As shown in FIG. 2 and in FIG. 3, in some embodiments an HPLC-based QCM 50 according to the present general inventive concept includes an HPLC pump 503, which draws mobile phase solvent from a mobile phase solvent reservoir 509 and through a degasser 504; a syringe-pump assembly 520 to load into the HPLC-based QCM 50 the sample radiopharmaceutical solution from a quality-control transfer line 400; an HPLC column 515; an injection valve 516; and fixed volume fluid loop 517. In some embodiments, including the example embodiment illustrated in FIG. 2, the HPLC-based QCM 50 according to the present general inventive concept includes a self-referencing radiation detector 544. Further, in some embodiments, the HPLC-based QCM 50 includes an UV/VIS detector 502 to test the optical qualities of the sample. In some embodiments, the HPLC-based QCM 50 includes an RI detector 505 to test the radionuclidic identity of the sample.

In the normal operation of the illustrated example embodiment of an HPLC-based QCM 50, as illustrated in FIG. 2, a sample radiopharmaceutical solution enters the syringe-pump assembly 520 from the quality-control transfer line 400. Within the syringe-pump assembly 520, the sample radiopharmaceutical solution is stored within a syringe 525. Then, the sample radiopharmaceutical solution is propelled by the syringe 525 or a similar mechanism and thereby is loaded, in a steady, even, and substantially reproducible manner, into a first QCM pathway 527. (In some embodiments, the syringe-pump assembly 520 draws mobile phase solvent from the mobile phase solvent reservoir 509.) The sample radiopharmaceutical solution moves through the first QCM pathway 527 and through a pH detector 501. In some embodiments, the pH detector includes a solid state detector. In some embodiments, the pH detector 501 includes an in-line solid state detector. The sample radiopharmaceutical solution moves beyond the pH detector 501 and passes through a first injection valve line 561 to enter the injection valve 516.

As illustrated in FIG. 2, there are six fluid-carrying lines that lead into or out of the injection valve: the first injection valve line 561, the second injection valve line 562, the third injection valve line 563, the fourth injection valve line 564, the fifth injection valve line 565, the sixth injection valve line 566.

The first injection valve line 561 conveys the sample radiopharmaceutical solution from the pH detector 501 (or, in alternate embodiments, directly from the syringe-pump assembly 520) into the injection valve 516.

The second injection valve line 562 conveys solution from the injection valve 516 to a card chemistry system (CCS) 545, which, in some example embodiments, includes at least one dose vial 534, a primary waste receptacle 557, and at least one test vial 521 to collect a sample aliquot for endotoxicity testing or other tests. In some embodiments, in the normal course of conducting quality control tests on the sample radiopharmaceutical solution, an aliquot of the sample radiopharmaceutical solution is tested for endotoxicity. In some embodiments, sample aliquot collected in the test vial 521 is tested for endotoxicity by diluting the sample aliquot and subjecting the diluted sample aliquot to an endotoxicity test. In some embodiments, the endotoxicity test is conducted by an automated endotoxin detector. In some embodiments, the endotoxicity test is conducted by an automated endotoxin spectrophotometer. In some embodiments, the endotoxicity test comprises the use of a kinetic hemocyte lysate-based assay for the detection and quantification of microbial contaminants. In some embodiments, other forms of endotoxicity tests are used.

The third injection valve line 563 conveys to the injection valve 516 mobile phase solvent drawn by the HPLC pump 503 from the mobile phase solvent reservoir 509 through the degasser 504. The fourth injection valve line 564 conveys fluid from the injection valve 516 to the HPLC column 515.

The fifth injection valve line 565 conveys fluid from the injection valve 516 into the fixed-volume fluid loop 517, and the sixth valve line 565 conveys fluid from the fixed-volume fluid loop 517 into the injection valve 516. Thus, three of the injection valve lines 561, 563, and 565 are input lines, and three of the injection valve lines 562, 564, and 566 are output lines.

In various embodiments, the injection valve 516 directs incoming fluid (generally the sample radiopharmaceutical solution or the mobile phase solvent) from an input line to an output line. Generally, the injection valve 516 is capable of being positioned in two different states. In the first state (also called State A), illustrated in FIG. 2, the injection valve 516 is positioned such that a channel within the injection valve 516 directs fluid from the first injection valve line 561 to the second injection valve line 562; that is, in State A, sample radiopharmaceutical solution passes from the pH detector 501, through the first injection valve line 561, through the injection valve 516, and then through the second injection valve line 562 to the CCS 545. In State A, mobile phase solvent from the HPLC pump 503 passes through the third injection valve line 563 into the injection valve 516. Within the injection valve 516, mobile phase solvent from the third injection valve line 563 is directed into the fifth injection valve line 565 and then into the fixed-volume fluid loop 517. The mobile phase solvent within the fixed-volume fluid loop 517 continues through the sixth injection valve line 566 back into the injection valve 516, where the mobile phase solvent is directed into the fourth injection valve line 564.

Figure 3:
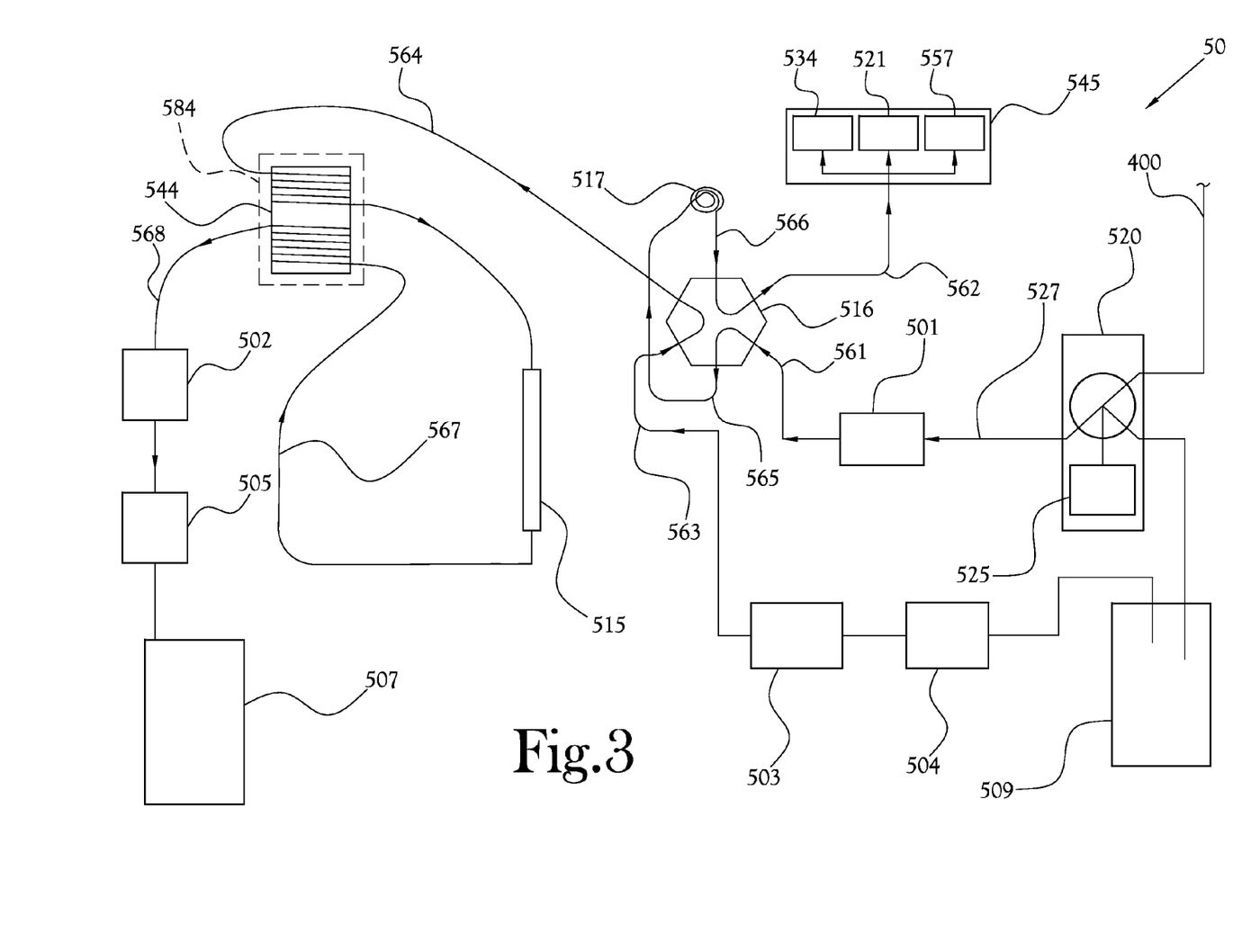
FIG. 3 is a second flow diagram illustration of the example embodiment of an HPLC-based QCM incorporating a self-referencing radiation detector shown in FIG. 2, showing an injection valve in a second state.

During the quality control testing process, at a point where sample radiopharmaceutical solution is flowing from the syringe-pump assembly 520 through the pH detector 501 and through the first injection valve line 561, the injection valve 516 is rotated 60 degrees into the second state (or State B), shown in FIG. 3. In State B, the sample radiopharmaceutical solution passes from the first injection valve line 561, through the injection valve 516, and then into the fifth injection valve line 565; from the fifth injection valve line 565, the sample radiopharmaceutical solution enters the fixed-volume fluid loop 517. As fluid continues to flow while the injection valve 516 is in State B, sample radiopharmaceutical solution flowing through the fixed-volume fluid loop 517 exits the fixed-volume fluid loop 517 and re-enters the injection valve 516 through the sixth injection valve line 566; the sample radiopharmaceutical solution is then directed into the second injection valve line 562, and the sample radiopharmaceutical solution passes through the second injection valve line 562 to the CCS 545.

While sample radiopharmaceutical solution is flowing through the fixed-volume fluid loop 517, the injection valve 516 is rotated a second time, so that the injection valve is again in State A (as in FIG. 2). At this point in time, mobile phase solvent from the HPLC pump 503 passes through the third injection valve line 563 and into the injection valve 516; within the injection valve 516, the mobile phase solvent from the third injection valve line 563 is directed into the fifth injection valve line 565. The mobile phase solvent within the fifth injection valve line 565 enters the fixed-volume fluid loop 517, pushing the sample radiopharmaceutical solution within the fixed-volume fluid loop 517 out of the fixed-volume fluid loop 517 and through the sixth injection valve line 566 into the injection valve 516. Within the injection valve 516, the sample radiopharmaceutical solution from the fixed-volume fluid loop 517 is directed into the fourth injection valve line 564. (In some embodiments, the fixed-volume loop 517 has a volume of approximately 20 microliters. However, those of skill in the art will recognize that other volumes the fixed-volume loop 517 are possible and are contemplated by the present invention.)

Conveyed along the fourth injection valve line 564, the sample radiopharmaceutical solution makes a pass by the self-referencing radiation detector 544. In some embodiments of the present general inventive concept, the fourth injection valve line 564—that is, the tubing within which the sample radiopharmaceutical solution is flowing—loops or coils around the self-referencing radiation detector 544 two or more times before proceeding to the HPLC column 515. The self-referencing radiation detector 544 acquires a first measurement of the activity of the sample radiopharmaceutical solution before the sample radiopharmaceutical solution enters the HPLC column 515; this first measurement provides the value for the activity of the bolus of sample radiopharmaceutical solution. Next, the bolus of sample radiopharmaceutical solution enters the HPLC column 515, where a number of components of the sample radiopharmaceutical solution are separated by their differing retention times into separate molecularly distinct components. The separate molecularly distinct components then elute from the HPLC column 515 after their distinct retention times. For each separate molecularly distinct component, the retention time of that component is noted. The separate molecularly distinct components eluted from the HPLC column 515 travel through a first post-separation line 567, which directs the separate molecularly distinct components past the self-referencing radiation detector 544. The self-referencing radiation detector 544 measures the activity of each separate molecularly distinct component to produce a raw activity measurement for that component.

Because the radioisotopes present in the sample radiopharmaceutical solution continue to decay while passing through HPLC column 515, the raw activity measurement for each molecularly distinct component is "corrected" by using the raw activity measurement for the component, the retention time for that component, and the half-life of the radioisotope to produce a decay-corrected activity value for that component. A comparison of the decay-corrected activity value for the separate components with the measured activity of the bolus of sample radiopharmaceutical solution provides a quantification of the radiochemical identity and radiochemical purity of the sample radiopharmaceutical solution.

In some embodiments, after the molecularly distinct components of the sample radiopharmaceutical are measured by the self-referencing radiation detector 544, the molecularly distinct components of the sample radiopharmaceutical pass through a second post-separation line 568 and through or past a UV/VIS detector 502 to test the optical clarity of the molecularly distinct components of the sample radiopharmaceutical solution. In some embodiments, the UV/VIS detector 502 comprises a ultra-violet and visible light spectrometer. In some embodiments, the UV/VIS detector 502 comprises a UV spectrophotometer. In some embodiments, the UV/VIS detector 502 comprises a UV spectrophotometer with a deuterium light source. In some embodiments, the UV/VIS detector 502 comprises a UV spectrophotometer with a tungsten-halogen light source. In some embodiments, the UV/VIS detector 502 comprises a UV spectrophotometer like the Smartline UV Detector 2500, manufactured by KNAUER. In some embodiments, the HPLC-based QCM 50 includes a detector comprises a spectrophotometer that detects a range of the electromagnetic spectrum that includes infrared light. In some embodiments, the HPLC-based QCM 50 includes multiple detectors, including, in some embodiments, multiple UV/VIS detectors or, in some embodiments, multiple spectrophotometers or spectrometers. In some embodiments, the UV/VIS detector 502 tests the sample radiopharmaceutical solution for the presence of residual Krypotofix. Generally, a purified radiopharmaceutical solution will be considered to pass quality control testing for Kryptofix if the residual concentration of Kryptofix in the final product is less than or equal to 50 micrograms per milliliter solution.

In some embodiments, the molecularly distinct components of the sample radiopharmaceutical solution pass through a refractive index detector (RI detector) 505. The RI detector 505 detects, measures and quantifies the presence of compounds. In some embodiments, RI detector 505 provides a measurement of the chemical purity of the sample radiopharmaceutical solution by providing a quantitative indication of the relative abundance of different separated molecularly distinct components within the sample radiopharmaceutical solution.

In many embodiments, the RI detector 505 also measures the residual concentration in the sample radiopharmaceutical solution of solvents such as acetonitrile and ethanol. Generally, a purified radiopharmaceutical solution will be considered to pass quality control testing if the residual concentration of acetonitrile in the sample radiopharmaceutical solution is less than or equal to 400 ppm.

Generally, after separate molecularly distinct components of the sample radiopharmaceutical solution are eluted from the HPLC column 515 and tested as described above, the separate molecularly distinct components of the sample radiopharmaceutical solution are conveyed to a secondary waste container 507.

Acquiring a measurement of radioactivity of each separate molecularly distinct species eluted from the HPLC column, and comparing the acquired measurements to the measured radioactivity of the sample radiopharmaceutical solution taken before the sample radiopharmaceutical solution entered the HPLC column, makes possible a calculation of the radiochemical identity and radiochemical purity of the sample radiopharmaceutical solution.

While the present invention has been illustrated by description of one embodiment, and while the illustrative embodiment has been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A system to test the radiochemical purity of a sample radiopharmaceutical solution, comprising:

a high performance liquid chromatography column to receive the sample radiopharmaceutical solution and to separate molecularly distinct species within the sample radiopharmaceutical solution into a number of separated molecularly distinct species;

a radiation detector, said radiation detector measuring the radioactivity of the sample radiopharmaceutical solution before the sample radiopharmaceutical solution is received by said high performance liquid chromatography column, said radiation detector measuring the radioactivity of each separated molecularly distinct species from said high performance liquid chromatography column; and a computer to operate a program to calculate a decay-corrected radioactivity measurement for each separated molecularly distinct species using the measurement of the radioactivity of each separated molecularly distinct species from said high performance liquid chromatography column, the half-life of a selected radioactive isotope within the radiopharmaceutical solution, and the time elapsed between measuring the radioactivity of the sample radiopharmaceutical solution before the sample radiopharmaceutical solution is received by said high performance liquid chromatography column and measuring the radioactivity of each separated molecularly distinct species from said high performance liquid chromatography column, whereby the radiochemical purity of the sample radiopharmaceutical solution is calculated by comparing the decay-corrected radioactivity measurements of the separated molecularly distinct species to the radioactivity measurement of the sample radiopharmaceutical solution.

2. A method to test the radiochemical purity of a sample radiopharmaceutical solution including a selected radioactive isotope, comprising:

acquiring with a radiation detector a radioactivity measurement of the sample radiopharmaceutical solution;

passing the sample radiopharmaceutical solution high performance liquid chromatography column to separate molecularly distinct species within the sample radiopharmaceutical solution into a number of separated molecularly distinct species that elute from said high performance liquid chromatography column with distinct retention times;

acquiring with said radiation detector an uncorrected radioactivity measurement for each separated molecularly distinct species eluted from said high performance liquid chromatography column; and calculating a decay-corrected radioactivity measurement for each separated molecularly distinct species using the uncorrected radioactivity measurement, the half-life of the selected radioactive isotope, and the time elapsed between the acquisition of the radioactivity measurement of the sample radiopharmaceutical solution the acquisition of the uncorrected radioactivity measurement for that separated molecularly distinct species, whereby the radiochemical purity of the sample radiopharmaceutical solution is calculated by comparing the decay-corrected radioactivity measurements of the separated molecularly distinct species to the radioactivity measurement of the sample radiopharmaceutical solution.

3. The method of claim 2 further comprising passing the separated molecularly distinct species through a refractive index detector to measure the amount of each separated molecularly distinct species eluted from said high performance liquid chromatography column.

4. The method of claim 2 further comprising passing the separated molecularly distinct species through an ultraviolet-light detector to measure the optical qualities of the separated molecularly distinct species eluted from said high performance liquid chromatography column.

5. The method of claim 2 further comprising passing the sample radiopharmaceutical solution through an ultraviolet-light detector to measure the optical qualities of the sample radiopharmaceutical solution.

6. The method of claim 2 further comprising a computer to operate a program to calculate the decay-corrected radioactivity measurement for each separated molecularly distinct species.

7. The method of claim 2 wherein the selected radioactive isotope is selected from the group consisting of carbon-11, nitrogen-13, oxygen-15, and fluorine-18.

8. The method of claim 2 wherein one of the separated molecularly distinct species eluted from said high performance liquid chromatography column is [$^{18}$F]-2-fluoro-2-deoxy-D-glucose.

* * * * *